United States Patent
Pedrizzetti et al.

(10) Patent No.: US 10,383,600 B2
(45) Date of Patent: Aug. 20, 2019

(54) METHOD FOR ANALYSIS AND DISPLAY OF BLOOD FLOW INFORMATION

(71) Applicants: TOMTEC IMAGING SYSTEMS GMBH, Unterschleissheim (DE); AMID S.R.L., Sulmona (AQ) (IT)

(72) Inventors: Gianni Pedrizzetti, Prato (IT); Giovanni Tonti, Sulmona (IT)

(73) Assignees: Koninklijke Philips N.V. (NL); Tomtec Imaging Systems GmbH (DE); AMID S.R.L. (IT)

( * ) Notice: Subject to any disclaimer, the term of this patent is extended or adjusted under 35 U.S.C. 154(b) by 928 days.

(21) Appl. No.: 14/614,953

(22) Filed: Feb. 5, 2015

(65) Prior Publication Data
US 2015/0335308 A1 Nov. 26, 2015

(30) Foreign Application Priority Data
Feb. 6, 2014 (DE) .................. 10 2014 202 150

(51) Int. Cl.
*A61B 8/08* (2006.01)
*A61B 8/06* (2006.01)
(Continued)

(52) U.S. Cl.
CPC .......... *A61B 8/5207* (2013.01); *A61B 5/0402* (2013.01); *A61B 8/06* (2013.01);
(Continued)

(58) Field of Classification Search
CPC ........... A61B 8/463; A61B 8/481; A61B 8/83; A61B 8/0883; A61B 8/461; A61B 8/5207;
(Continued)

(56) References Cited

U.S. PATENT DOCUMENTS

| 5,634,465 A | 6/1997 | Schmiesing et al. |
|---|---|---|
| 2008/0015440 A1 | 1/2008 | Shandas et al. |

(Continued)

FOREIGN PATENT DOCUMENTS

WO 2013059659 A1 4/2013

OTHER PUBLICATIONS

Sengupta et al "Emerging Trends in CV Flow Visualization" J. Am. Coll. Cardiol. Img. 2012 vol. 5, No. 3, pp. 305-316.
(Continued)

*Primary Examiner* — Bo Joseph Peng

(57) ABSTRACT

A method and a device for analysis and display of blood flow information in the human or animal body are described. The method includes the following steps:
a) providing a digital input data set including a time series of two or three dimensional velocity vector fields, wherein each velocity vector field represents the velocity of the blood flow within a blood vessel, especially of a heart chamber or part thereof, of a certain human or animal body within a certain time frame within one heart cycle,
b) calculating a gradient vector field for each time frames from the time series of velocity vector fields;
c) summing the gradients over the gradient vector field or a part thereof for each time frame to a summed gradient; and
d) displaying and/or analyzing the summed gradients with reference to their space directions within the blood vessel.

22 Claims, 5 Drawing Sheets

(51) Int. Cl.
  *A61B 8/14* (2006.01)
  *A61B 5/0402* (2006.01)
  *A61B 8/00* (2006.01)
  *G06T 7/269* (2017.01)
  *A61B 5/055* (2006.01)
  *A61B 5/00* (2006.01)

(52) U.S. Cl.
  CPC .............. *A61B 8/0883* (2013.01); *A61B 8/14* (2013.01); *A61B 8/461* (2013.01); *A61B 8/488* (2013.01); *A61B 8/5223* (2013.01); *A61B 8/5284* (2013.01); *G06T 7/269* (2017.01); *A61B 5/055* (2013.01); *A61B 5/7425* (2013.01); *A61B 8/463* (2013.01); *A61B 8/481* (2013.01); *A61B 8/483* (2013.01); *G06T 2207/10016* (2013.01); *G06T 2207/10136* (2013.01); *G06T 2207/30104* (2013.01)

(58) Field of Classification Search
  CPC ....... A61B 8/5223; A61B 8/5284; A61B 8/06; A61B 8/14; A61B 5/0402; A61B 5/055; A61B 5/7425; G06T 7/269; G06T 2207/10016; G06T 2207/10136; G06T 2207/30104

See application file for complete search history.

(56) References Cited

U.S. PATENT DOCUMENTS

| | | | |
|---|---|---|---|
| 2012/0265075 A1* | 10/2012 | Pedrizzetti | A61B 8/06 600/454 |
| 2013/0137987 A1 | 5/2013 | Abe et al. | |
| 2016/0354269 A1 | 12/2016 | Fouras et al. | |

OTHER PUBLICATIONS

Munoz et al "Intracardiac Flow Visualization:Current Status and Future Directions" European Heart Journal, Cardiovascular Imaging Aug. 1, 2013.

Lang et al "Recommendations for Cardiac Chamber Quantification by Echocardiography in Adults" An update from the American Society of Echocardiography and the European Association of Cardiovascular Imaging, Journal of the American Society of Echocardiography 2015, Vo. 28, No. 1, pp. 1-39.

* cited by examiner

METHOD FOR ANALYSIS AND DISPLAY OF BLOOD FLOW INFORMATION

TECHNICAL FIELD

The invention relates to a method and a device for analysis and display of blood flow information in the human or animal body.

BACKGROUND

The blood flow in the human heart is very intricate, and it is presumed that the fluid dynamics in the heart are greatly influenced by even minor changes of the cardiovascular function. For example, vortices in blood flow contribute to the dynamic equilibrium between the hyperelastic heart tissue and the intraventricular blood pressure and the shear stress. The vortices are likely to be critical to the energetic properties of the blood flow. Heart function and quality of the intraventricular fluid dynamics are presumed to be closely related. Dilatation or dyskinesia could result in distortion of vortex, local stagnation and reduced flow exchange accompanied by higher risk of thrombus formation. Changes in fluid dynamics, e.g. changes of vortex or eddies as well as partially reversed blood flow movement are likely to be an early indicator of changes of the heart function, even before they become manifest in the heart muscle itself.

Possibly, more specific analysis of the blood flow may hence provide essential information concerning the heart function. Nevertheless, cardiovascular fluid dynamics are rarely utilized in everyday clinical practice, especially since technical means for the examination thereof are missing. Hence, there is a demand for new techniques for the examination of fluid dynamics of the heart function.

Medical imaging methods for displaying large blood vessels or heart chambers are for example Phase Contrast Cardiac Magnetic Resonance (CMR), by which a three dimensional (3D) velocity vector field may be achieved. However, this method does not provide optimal space resolution nor acquisition frequency, and the results must be averaged over a large number of heartbeats, so that minor fluctuations e.g. in vortex/eddy formation, are not detected.

An alternative is the Ultra Sound Color Doppler, which however shows the basic limitation that solely the component of the blood flow parallel to the ultra sound beam is detected. In order to overcome this limitation, methods have been developed for reconstructing a velocity vector field from the color Doppler velocity information (refer to US 2012/0265075 A1).

A more versatile echocardiographic technique for imaging and evaluating the blood flow in the large vessels or in the heart, respectively, in real time is known under the name of Echo-PIV (Echo particle image velocimetry). This technique is for example described in the articles of P. P. Sengupta and G. Pedrizzetti et al. "Emerging Trends in CV Flow Visualization", J. Am. Coll. Cardiol. Img. 2012; Vol. 5; No. 3; pp. 305-316, as well as D. R. Munoz, M. Markl et al. "Intracardiac flow visualization: current status and future directions", European Heart Journal—Cardiovascular Imaging, 1 Aug. 2013, doi:10.1093/ehjci/jet086. The contents of these documents are enclosed in this application.

The Echo-PIV technique is based on that a time series of 2D (two dimensional) or 3D (three dimensional) ultra sound images of the heart is recorded. Generally, acquisition over one single heartbeat is sufficient, since the time resolution is very high. During this procedure the patient may have also been given a suitable ultra sound contrast agent. In post-processing, the individual particles visible in the blood (e.g. reflecting particles of contrast agent) are traced from image to image. In doing so, velocity vector fields may be calculated and visualized, such as e.g. represented in FIG. 1. This may be done both in 2D and 3D. In 2D ultra sound images solely the blood flow in the image plane is detected. By "ultra sound image" in this application especially a B mode image is understood, if not stated otherwise.

BRIEF SUMMARY

The present invention provides a method and a device for analysis of the blood flow of the large blood vessels, especially of the human or animal heart. It is required that the methods are applied easily, as non-invasive as possible, and provide clinical indicators for the fluid dynamics in the heart or other large blood vessels which are to be analyzed with maximum ease.

DESCRIPTION OF THE EMBODIMENTS OF THE INVENTION

As an input data set the method uses a time series of two or three dimensional velocity vector fields, each of which vector field depicting the velocity of the blood flow within a blood vessels, especially of a heart chamber or part thereof of a certain human or animal body within a certain time frame within a heart cycle. Thus, by a velocity vector field a data set comprising a 2D or 3D matrix of pixels or voxels, respectively, is to be understood, wherein for each pixel or voxel position, respectively, a vector is deposited, which represents the velocity of the blood flow at a certain location in the heart. There are several velocity vector fields, which each depict the blood flow in a different time frame within a heart cycle, wherein e.g. 10-50 time frames per heart cycle are depicted, depending on the time resolution of the medical imaging method, by which the images were acquired, from which the input data set was reconstructed. Preferably, the input data set is reconstructed by way of Echo PIV from a time series of ultra sound images of the heart. They may be 2D image data or 3D image data. Accordingly, the calculations of the gradient vector fields (also refer to mathematical background) may be performed either in 2D or 3D. The heart chamber may be the right or left ventricle or the right or left atrium, the left ventricle being preferred.

Alternatively, the input data set may also be acquired from magnetic resonance tomography images or by reconstructing a velocity vector field from 2D or 3D ultra sound color Doppler images.

According to one embodiment, the method also comprises the step of acquiring a time series of ultra sound images of a blood vessel, especially a heart chamber, of a certain human or animal body. Preferably, an ECG is simultaneously be performed, to allow allocation of each of the ultra sound images to a certain point of time in the heart cycle. It is preferred that a time series of velocity vector fields will then be determined from these images by way of Particle Image Velocimetry. The ultra sound images and the velocity vector fields reconstructed therefrom may be 2D or 3D. In one embodiment, a time series of one, two or three or more 2D ultra sound images depicting different slices though the blood vessel or heart is acquired, from which accordingly a time series of one, two or three 2D velocity vector fields are reconstructed. The 2D ultra sound images are preferably oriented along the long axis (main direction of the blood flow) of the left ventricle, one of the 2D images in the time series may e.g. acquired from a so called three chamber view.

A gradient vector field, preferably a pressure gradient vector field, is calculated from the time series of velocity vector fields for each of the time frames. Further embodiments and detailed information for calculation will be given further below. It is of advantage, that the spatial distribution of specific gradients, e.g. the pressure gradient, may be determined and analyzed over a heart chamber.

For each of the time frames, the gradients are then preferably summed up to a summed up gradient over a gradient vector field or part of the same. Thereby, within each time frame, the gradients are spatially integrated or summed up, i.e. the gradients stored for each pixel/voxel location in the gradient vector field belonging to one time frame are summed up. If only part of the gradient vector field is summed up this part should either cover a certain blood vessel or heart chamber, or the heart chamber is divided into several sections, which are to be analyzed separately, and the gradients are each separately summed up for each section. However, it is preferred that the gradients are each summed up over an entire heart chamber to a summed gradient. However, this is preferably done individually for each the time frame, so that as a result of this step there is a time series of summed gradients, i.e. one gradient vector for each time frame representing the sum of all gradients in the blood vessel within this time frame.

The time series of summed gradients are finally displayed and/or analyzed in relation to their space directions within the blood vessel or the heart chamber.

The method of the invention may e.g. advantageously be employed in so called CRT (Cardiac Resynchronisation Therapy), where it is crucial to stimulate the heart muscle by a pace maker such that it simultaneously contracts—in non-simultaneous contraction e.g. pressure or momentum gradients transversally to the inflow and outflow direction of the blood pressure are generated, which may result in stress and eventual pathological deformation (remodeling) of the heart. The inflow direction into the left ventricle is e.g. through the mitral valve in the base in the apex direction. The outflow direction is from the apex into the aortic valve direction at the base. Thus, the gradients should be towards the apex-base direction, gradients which are transversally directed thereto are pathologic. Such gradients may be visualized by the method of the invention. Preferably, the display is in real time, i.e. within 1-5 seconds following acquisition of the ultra sound images, from which the input data set was generated. This allows e.g. performance of the blood flow within a heart chamber to be taken into account in adjusting heart pacemakers for treatment of CRT.

The summation of the gradient vector field according to its direction preferably allows analysis of the intensity-weighted frequency of such a gradient field in this direction.

It is preferred that the summed gradients of all time frames of a heart cycle are displayed in one single diagram and/or are suitably analyzed. In another embodiment only the summed gradients of the time frames belonging to the systole or diastole are displayed in a diagram. For example for each one of the systole and diastole a diagram may be generated.

To be able to correlate the summed gradient to the space orientation of the blood vessel or the heart chamber, one or more "normal" images of the blood vessel is preferably analyzed by segmentation into blood and tissue of the vessel wall or the heart chamber wall. This may be a static image or a time series of images covering one heart cycle. It is preferred to use the ultra sound images from which also the input data set was reconstructed by way of Echo PIV. In doing so, it is possible to determine the course of the tissue heart chamber wall, and one can then find out towards which space direction within the blood vessel (e.g. base or apex direction, direction of specific heart valves) the gradients or summed gradients are directed. In doing so, it is possible to represent the course of the tissue or heart chamber wall, respectively, in 2D or 3D, e.g. a long section through a heart chamber, and to correlate the summed gradients as arrows, bars or in another depiction with this, so that by way of a straightforward display it becomes clear, if the gradients, for example the pressure slope, within the heart chamber is normal or deviant. Especially the angles between the summed gradients and the tissue or heart chamber wall, respectively, may be analyzed.

There may be calculated different gradients, especially the pressure gradient, the blood flow kinetic energy gradient, the momentum gradient, the momentum, the convective portion of the momentum, the inertia portion of the momentum, the inertial acceleration gradient or the blood flow convective acceleration gradient. This shall preferably be calculated for each time frame or for each one of the changes between two time frames, for which a velocity vector field is provided. By "gradient vector field" a vector field of any vector size is understood, which may be calculated from the velocity vector fields, such as for example the momentum of blood flow.

The pressure gradient vector field is for example calculated by a) calculating the derivative with regard to time of the velocity vector fields from one time frame to the next and storing the result as a time series of acceleration vector fields, b) for each time frame, calculating the scalar product between the velocity vectors and the velocity gradients at each point and storing the result a, and c) summing up the calculated vector fields, optionally with desired relative weights.

Mathematically expressed, the pressure gradient vector field is calculated by solving the pressure Poisson equation with appropriate boundary conditions. This is expressed as follows:

The equation of momentum balance for an incompressible fluid, ignoring viscous effects, reads in general as $$\nabla p = -\rho\left(\frac{\partial v}{\partial t} + v \cdot \nabla v\right);$$

where v(x,t) is the fluid velocity vector that takes a value at every point, x, and at every instant, t, and p(x,t) is the pressure (scalar). The symbol ρ is the fluid density (a constant that for blood is approximately equal to 1050 Kg/m$^3$). The previous equation is known as Euler equation (or Navier-Stokes equation without viscosity). It explains that the pressure gradient, ∇p, (a vector) is composed by two terms: the first one is computed from the time derivative of the velocity vector, $$\nabla p = -\rho\left(\frac{\partial v}{\partial t} + v \cdot \nabla v\right);$$

that is a vector as well; the second one is computed by the scalar product of the velocity vector, v, and the velocity gradient ∇v that is a matrix (2×2 in 2D field, or 3×3 in a 3D field), the scalar product between a vector and a matrix produces a vector. In the 3D-case, the velocity gradient ∇v can be calculated from the velocity vector v by $$v = (v_x, v_y, v_z);$$

$$\nabla v = \begin{pmatrix} \frac{dv_x}{dx} & \frac{dv_x}{dy} & \frac{dv_x}{dz} \\ \frac{dv_y}{dx} & \frac{dv_y}{dy} & \frac{dv_y}{dz} \\ \frac{dv_z}{dx} & \frac{dv_z}{dy} & \frac{dv_z}{dz} \end{pmatrix}$$

Therefore, from the velocity field, its time derivative and its gradient, the pressure gradient can be estimated for each pixel/voxel of the input data set, thus a new vector field is calculated for each time frame. The vectors within each vector field are summed up or spatially integrated, possibly with different weights at different spatial positions, over the blood vessel, in order to generate a summed gradient for each time frame. If the calculated vector field represents the pressure gradients (as explained above), the summed gradient is the global hemodynamic force vector.

The global hemodynamic force vector can be computed, at every instant, by spatial integration of the pressure gradient on the entire chamber (usually the left ventricle, LV)

$$F(t) = \int_{LV} \nabla p \, dS.$$

where dS is the infinitesimal space over which the integral is performed. The integral is a symbolic expression to indicate the summation of the values of pressure gradient at all points that are computed as described above. The summation can include different weights at different points to best approximate the integral depending on the specific quadrature formula used. Typically, values close to boundaries have smaller weights than values in the central regions because they influence a smaller region of fluids. Weights can also take into account the accuracy in the estimation of the pressure gradient, thus giving larger weights to values that can be considered more reliable.

In another embodiment, the calculated gradient vector field may represent the momentum. The momentum as a "gradient" is of advantage, since it allows visualization of the interaction between blood and tissue. Momentums which are directed toward the lateral walls of a ventricle, may with time lead to pathological protrusions (remodeling). The invention allows for the detection of such flow imbalances and thus introduction of therapy, before pathological heart deformations occur.

The momentum may be obtained by multiplication of the velocity vector by an average density of blood.

The gradient vector field of kinetic energy is preferably calculated by squaring the velocity vectors and derivation with respect to place and/or time.

There are different approaches for displaying the summed gradients, especially those of all time frames of a heart cycle in one single diagram. Especially preferred is the display in a polar diagram, wherein the polar angles of the polar diagram correspond to specific space directions of the heart chamber. This display is similar to that of a wind rose.

According to an advantageous embodiment, a polar diagram is established for each time series of 2D velocity vector fields. The polar angle of the polar diagram corresponds to the direction of the represented vector (especially gradient vector) within the image plane, and the radial coordinate (distance from the pole) corresponds to the modulus of the vector.

Each of the summed gradients may now be displayed, e.g. as a dash, arrow or point starting from the center (pole) of the polar diagram towards the respective direction, wherein the length of the dash or arrow or distance of the point from the origin corresponds to the size (modulus) of the gradient.

Additionally, the ends of the dashes/arrows or points, respectively, may be connected to each other, preferably in the sequence in which they occur within the time series, so that it will become obvious to the viewer how the summed gradients rotate in the course of the heart cycle. The pressure gradient in a normal left ventricle in the diastole should for example point from the mitral valve towards the apex, and subsequently, during the systole, should point towards the direction of the aortal valve.

In order to average out noise or inaccuracies in the gradient, it is possible to divide the angles of the polar diagram into segments and to plot the sum of all summed gradients, the angles of which fall into this segment, as bars in each segment. In the case of the polar diagram the bar then preferably has the form of a wedge (like the segment of a pie chart), as shown in FIGS. 4a and 4b. This is called a polar histogram, and can be mathematically described as follows:

The force vector F(t) can be divided into its components. Considering a 2D vector, the two components can be expressed as $F_1(t)=F \times \cos \theta$ and $F_2(t)=F \times \sin \theta$, respectively, where $F(t)=(F_1^2+F_2^2)^{1/2}$ is the modulus of F, and $\theta$ (t) the angular orientation (polar angle). For creating a polar histogram of the force during a time frame, the circumference is divided in N sectors, centered in $\theta_i=(2i-1)\pi/N$, i=1 ... N, where N may for example be between 8 and 16 or 24, preferably 12, and the moduli of the force vectors during the various time instants are summed up when the angle falls in a corresponding sector. Alternatively, the force vectors falling into each segment are summed by vector summation and the modulus is then taken. In an embodiment, the resulting N values, $A_i$ are normalized to unit sum to provide an intensity-weighted angular frequency distribution, i.e. showing how often during the heart cycle the summed gradient points in a particular direction. The N values $A_i$ are then depicted in the polar diagram by a bar or otherwise.

Alternatively, instead of a bar a shade may be used, either in grey shades or color. The polar diagram then is for example a ring, the color of which indicates each one of amount or strength, respectively, of the summed gradients, which point towards the respective direction of the polar angle.

In addition to or superimposed to the diagram (polar diagram or polar histogram), in which the gradients are displayed, the contour of the heart chamber, especially the boundary between blood filled interior space and heart chamber wall, may be displayed. This may either be performed in a three dimensional manner, e.g. such as pericardium display (refer to EP 0 961 135 A1 of the applicant). Alternatively, a sectional image may be displayed with this contour, especially a sectional image, which corresponds to the image plane of a 2D image, from which the velocity vector fields were reconstructed, or a plane, onto which the display of the summed gradients is projected.

In one embodiment the input data set is achieved from one or more (e.g. 2-3) 2D ultra sound images, which each are oriented along the long axis of the left ventricle. One of these planes is for example the "three chamber view". In each of these cases 2D velocity vector fields are reconstructed, which display the blood flow in the 2D image plane. For each 2D image plane a polar diagram, such as described above, may be established.

Alternatively, from 3 or more 2D image planes, which are oriented along the long axis, a standard polar diagram may also be established. This is a display of the wall of the left ventricle projected onto a circle and divided into predefined segments, wherein the apex is in the center. The color shade of this diagram then displays the modulus of the summed gradients which point towards the direction of this segment. This schematic 2D representation of the left ventricle wall is called "bull's eye" and is described in the article by Roberto M. Lang et al. "Recommendations for Cardiac Chamber Quantification by Echocardiography in Adults: An Update from the American Society of Echocardiography and the European Association of Cardiovascular Imaging", Journal of the American Society of Echocardiography 2015; Volume 28 No. 1; pp. 1-39, the content of which is hereby incorporated by reference.

To achieve a three dimensional display, the three dimensional space directions of the summed gradients which are to be displayed may also be displayed in two polar diagrams, each polar diagram corresponding to the space directions of the heart chamber projected to plane. Preferably, herein the planes also extend through the long axis of the heart chamber, but for example offset to each other by a 90° angle.

In the case of 3D velocity vector fields, according to one embodiment, each of the summed gradients are advantageously projected onto a plane through the heart chamber, wherein this plane in the case of the right ventricle preferably extends through the base and apex. Generally, with blood vessels or heart chambers, a plane is useful which extends through the long axis of the vessel. In other words, the angles of the polar diagram correspond to the space directions of the heart chamber projected onto a plane, wherein the long axis of the chamber extends in the plane.

Alternatively, in case of 3D velocity vector fields, a 3D histogram can be generated, analogously to the polar diagram for the 2D case explained above, wherein instead of the polar angle $\theta$ the angles $\theta$ and $\varphi$ of the spherical coordinate system are used. The summed gradients for each segment can be displayed e.g. in a 3D histogram, or in a "Bull's Eye" diagram as described above, where the segments of the "Bull's Eye" are colored or shaded to show the intensity of the summed gradients pointing to this segment. To do this, the spherical coordinates $\theta$ and $\varphi$ are divided into segments, and each segment is allocated to a segment of the standard "Bull's Eye" diagram.

To analyze the dynamics of the gradients, it is also possible to sequentially display the summed gradients of all time frames in their order during the heart cycle in one and the same diagram, i.e. in an animated display. Otherwise the display may correspond to the embodiments described above, except that not all summed gradients are displayed simultaneously.

Moreover, the display of the summed gradients of all time frames may also be done in a histogram, wherein different solid angle segments of the heart chamber are plotted onto the x-axis.

Instead of the gradients of which each is summed over the entire heart chamber, the gradients of the gradient vector fields may also be directly visualized in the above described manner, e.g. if it is desired to watch the space distribution of the gradients in a specific heart chamber in a specific time frame in the heart cycle.

Instead of gradient vector fields, other parameter characterizing the fluid dynamics in a blood vessel or a heart chamber, respectively, may also be calculated from the time series of velocity vector fields. Especially, this may be the kinetic energy, the energy dissipation and/or shear stress of the blood flow, which preferably is calculated for each time frame from the time series of velocity vector fields. Thus the space distribution of these parameters within the heart chamber is known.

According to one embodiment, these parameters are also summed over the gradient vector field or part of the same for each time frame, in order to especially summarize over the entire vessel or a section of the vessel, respectively, as described above.

These parameters then are also preferably interrelated to the contours of the blood vessel or the heart chamber, respectively, and/or their change is analyzed or displayed in the course of the heart cycle.

According to one embodiment, these (scalar) parameters may be plotted onto a pericardium display of the heart as grey values or preferably according to a color scale. A display of the inner contour of a heart chamber as a pericardium is especially described in EP 0 961 135 A1. It is a wire frame model of the boundary between internal space and endocardium, which preferably is established for each time frame within the heart cycle and for example is displayed in an animated manner.

Alternatively the parameters may also be inputted into e.g. a known polar plot display of the right or preferably left ventricle, wherein the endocardium of the ventricle is divided according to a specific scheme into radial sections and are projected onto a plane and are displayed as polar plot ("Bull's Eye"). A display in two polar plot diagrams is also conceivable, which each represent the left ventricle from the apex to the base or from the base to the apex, respectively.

Moreover the parameters may also be displayed as a function of time over the heart cycle.

Moreover, the parameters may also be displayed parametrically in a graphical long or short axis display of a heart chamber.

The invention also pertains to a computer program having the appropriate program code which executes the method described above, if the program is executed on a computer.

Moreover the invention also pertains to a non-transitory data storage device, for example a hard disc, a CD-ROM, a RAM memory, an optical data storage device, or an USB stick, where a computer program for performing the method described above is stored.

Finally, the invention also comprises a device for performing the method described above. The device especially comprises a data storage device, which at least stores the digital input data set. Moreover it also preferably stores the calculated gradient vector fields for each time frame as well as the other calculated parameters. Furthermore, there is a processing unit, especially part of a computer or mobile device, e.g. a CPU or another digital processing unit. It calculates the gradient vector fields and/or other remaining above mentioned parameters from the time series of velocity vector fields.

Finally, it is preferred that there is an image screen, which is suitable for displaying the summed gradients in relation to their space directions within the blood vessel, and/or the remaining above mentioned parameters, as described above.

The device may also be standalone, and may e.g. a commercially available PC or a work station. It may also be part of an ultra sound acquisition device, with which the ultra sound images are acquired, from which the velocity vector fields are reconstructed.

Mathematical Background

The kinetic energy of a heart chamber is defined as being the half of the squared velocity, integrated or summed up over the entire blood in the ventricle, respectively. The kinetic energy characterizes the global fluid-mechanical performance of the heart chamber, especially the left ventricle, and is a prospective additional clinical indicator of the heart function. The space distribution of the kinetic energy, which also may be calculated by the present method provides information about the regions of the heart, which are involved in the transfer of muscle work into blood energy, and hence may indicate the presence of ischemic regions. The kinetic energy summed up over the heart chamber is an intrinsic measure of energy for the flow, which may be related to volume measures, such as e.g. the beat volume (stroke volume) or the ejection fraction, since the kinetic energy correlates to the momentum transfer as well as mass conservation. In a straight canal, e.g. of a straightly extending arteria, the kinetic energy is equivalent to the beat volume and heart frequency; in a complex and turbulent blood flow the same beat volume may be transferred in an efficient or less efficient manner to the blood flow. Hence, the kinetic energy represents an energetic measure, which is integrative or even substitutive in relation to analogous parameters, which only are given by mass equilibrium. The kinetic energy represents the essential energetic property of the blood flow in the left ventricle.

In addition, the measure for dissipation of the kinetic energy may be calculated, characterizing the regularity or evenness of the chamber activity. In addition, space fluctuations of the kinetic energy within the heart chamber and the vector products of velocity components (Reynolds shear stress) represent an additional measure of quality of the blood flow and the level of turbulence in the heart chamber. The global and local evaluations of the kinetic energy are performed by consideration of the vortex chirality, so that each quantification is provided with the local flow rotation (vorticity). In some pathologies or after therapy it may dramatically change or may even go into reverse. Energetic properties characterize the quality of work of the heart chamber, especially of the left ventricle. High dissipation, low efficiency and high turbulence may all be preliminary indicators for the heart's tendency to deform: the first step of eclectic pathology of heart failure.

From a dynamic point of view, the intraventricular pressure gradients (intraventricular pressure gradients, IVPG) may be calculated from the velocity vector field. This is done by solving a Poisson's equation, which results from the Navies-Stokes equations, especially after divergence has been taken:

The Navies-Stokes vector equation for an incompressible fluid is:

$$\nabla p = \rho \frac{\partial \vec{v}}{\partial t} + \rho(\vec{v}\cdot\nabla)\vec{v} + \rho\nu\nabla^2\vec{v},$$

and it is combined with the condition of incompressibility, i.e. that the divergence of the velocity vector field equals 0:

$$\nabla\cdot\vec{v}=0.$$

Taken the divergence, the following equation, named Poisson equation, results for the pressure p:

$$\nabla^2 p = \nabla\cdot(\vec{v}\cdot\nabla\vec{v}),$$

wherein the right side may be calculated from the known velocity vector field. This linear equation may numerically be solved with known algorithms (Fast Poisson Solvers) numeric with different techniques, e.g. with finite differences, finite elements and limit value methods.

The solution requires boundary conditions, e.g. Neumann boundary conditions at the tissue wall and Dirichlet conditions at sections transversal to the flow, e.g. inlet and outlet valves (refer to e.g. Ebbers T, Wigstrom L, Bolger A F, Wranne B, Karlsson M. "Noninvasive Measurement of Time-Varying Three-Dimensional Relative Pressure Fields Within the Human Heart." Journal of Biomechanical Engineering 2002; 124:288-293). Alternatively the Poisson equation may also be solved under homogenous boundary conditions.

The Poisson equation may be solved, provided that the velocity vector field v is known and the pressure field p is a relative one. In the solution the boundary conditions are preferably set to zero. This is especially possible, since the velocity vector field generally is larger than the heart chamber itself, so that it may be taken into account, that the blood flow at the edges of the vector field equals zero.

Since the Poisson equations second degree, the solution is defined, even besides a bilinear function, which is obtained by way of appropriate boundary conditions or by way of further use of the Navier-Stokes equations.

If the space distribution of the relative pressure is known, on the one hand, a pressure gradient vector field may be calculated.

Furthermore, the pressure difference between the base and apex of the left ventricle may be calculated, which e.g. depicts physiological details of the blood flow in the left ventricle, e.g. the pre-diastolic suction capacity of the left ventricle, which is reduced under pathological conditions, or the elastic resilience in the view of fluid dynamics. The pressure gradients may be calculated as a 2D or 3D vector field. The deviation of the pressure gradient in the base to apex direction, in other words the direction of the long axis, is influenced by vortices and the elastic resilience of the tissues, and reflects global and local changes in the fluid-tissue interaction. Deviations from the direction of the long n axis result in increase of pressure to the segments parallel to the long axis of the heart muscles and may there result in an "remodeling" effect.

The distribution of the intraventricular pressure gradients may be evaluated by measuring the intensity and time period along specific directions to generate diagrams and histograms as well as indices of their strength and orientation.

The intraventricular pressure gradients are forces that are transferred sections via the incompressible medium of blood from one section of the endocardium tissue of the ventricle to other. Therefore, transversal intraventricular pressure gradients may be interpreted as respective work of the myocardium exerting pressure on the opposite tissue element, instead of promoting the evacuation process of the ventricle. This represents continuous hammering which possibly is co-responsible for a dysfunctional deformation of the heart chamber.

The momentum may for example be calculated by known algorithms from the following formulas:

The inertia component I of the momentum is as follows:

$$\vec{I} = \rho \frac{\partial \vec{v}}{\partial t};$$

wherein ρ is the density of the blood (normally is ρ=1050 Kg/m3) and v is the velocity (of the velocity vector field). The convective (or advective) component is as follows:

$$\vec{M} = \rho(\vec{v} \cdot \nabla)\vec{v};$$

The convective component M may furthermore be divided into two parts $M=M_1+M_2$, of which one ($M_1$) is related to the kinetic energy and the other one ($M_2$) is related to the rotation of the fluid.

$$\vec{M}_1 = \nabla E;$$

$$\vec{M}_2 = \vec{v} \times (\nabla \times \vec{v});$$

Each one of the individual components of the momentum are vectors having intensity (or amount) and direction. The quantification of the invention or the calculation of one of the vectors as gradient vectors or of the sum thereof corresponds to the momentum that collects the blood due to interaction with the surrounding tissue, e.g. the heart chamber wall, and the momentum that is available to the blood for the transfer onto the tissue. This is the blood-tissue interaction.

The kinetic energy E is a field that is given by the definition $$E(\vec{x}, t) = \frac{\rho}{2} \|\vec{v}\|^2,$$

and that may be expressed in a 2D velocity field as follows $$E(x, y, t) = \frac{\rho}{2}(v_x^2 + v_y^2),$$

Herein, ρ is the density of the blood and v is the velocity. The energy available at a certain point of time then is the integral over the E-field within a blood vessel, especially of a heart chamber.

The rate of the energy dissipation is defined as (chap. 13, p. 106 in: Kundu P K, Cohen I M, Fluid Mechanics, $3^{rd}$ edition. Elsevier Acad. Press, San Thego, Calif., USA, 2004)

$$D(\vec{x}, t) = 2\rho v \sum_{i,j=1}^{3} S_{ij} S_{ij};$$

wherein S is the deformation tensor, the symmetrical part of the velocity gradient:

$$S_{ij} = \frac{1}{2}\left(\frac{\partial v_i}{\partial x_j} + \frac{\partial v_j}{\partial xi}\right);$$

The Rate of the energy dissipation, in a 2D velocity vector field, becomes $$D(x, y, t) = \rho v \left\{ 2\left(\frac{\partial v_x}{\partial x}\right)^2 + 2\left(\frac{\partial v_y}{\partial y}\right)^2 + \left(\frac{\partial v_x}{\partial y} + \frac{\partial v_y}{\partial x}\right)^2 + \left(\frac{\partial v_x}{\partial x} + \frac{\partial v_y}{\partial y}\right)^2 \right\};$$

Herein, ρ is the density of the blood (normally ρ=1050 Kg/m3) and v is the kinematic viscosity (for blood approximately v=3.3×10−6 m2/s). $v_x$, $v_y$, $v_z$, are the components of the velocity of the velocity-vector field. Then, the entire energy dissipation is the integral of the D field over the area within a heart chamber, especially within the left ventricle, and over the duration of one heart beat T.

The shear stress is the transversal gradient of the velocity v, representing the friction. In a Newtonian fluid the stress tensor T is proportional to the deformation tensor S (refer to the above), with the constant of proportionality of the viscosity v and the density ρ:

$$\vec{T} = -2\rho v \vec{S}.$$

Shear stresses are the non-diagonal values of this tensor T. In the simple case of a stream flowing along the direction x the shear stress τ is given by the differential velocity of the fluid elements, calculated as follows $$\tau = -\rho v \frac{\partial v_x}{\partial y};$$

wherein y is a direction transversally to the flow, and T is one of the non-diagonal components of the stress tensor $\tau = T_{xy}$.

BRIEF DESCRIPTION OF THE DRAWINGS

FIG. 1A shows the flow pattern represented by a 2D flow line on a longitudinal plane, and FIG. 1B shows flow pattern represented by a 3D flow lines;

FIG. 2A shows representation of the velocity vector field through the left ventricle at systole, and FIG. 2B shows representation of the velocity vector field through the left ventricle at diastole;

FIG. 4A shows the representation for a normal heart;

FIG. 4B shows the representation in a pathological heart;

DETAILED DESCRIPTION

Figure 1A:
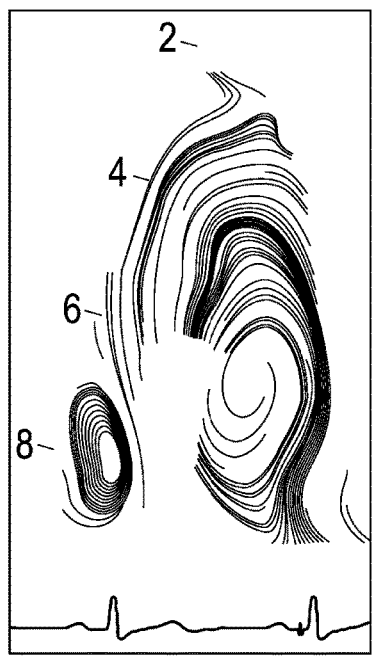
FIGS. 1A-1B are representations of the intraventricular velocity vector field at end of diastole, as reconstructed by way of Echo-PIV from echocardiographic records from the apex.
Figure 1B:
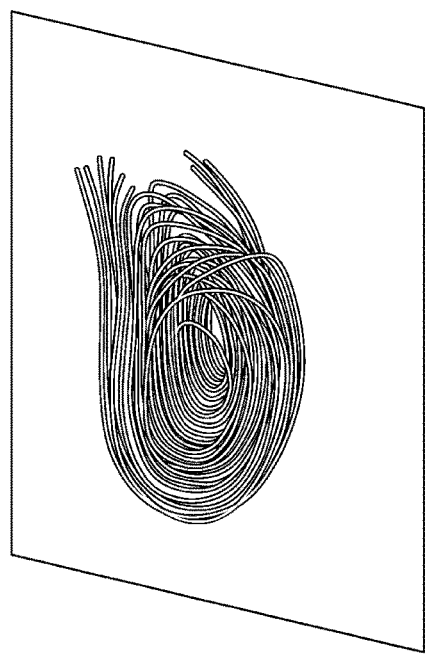

FIGS. 1A-1B show a visualization of Echo-PIV images, wherein each one of the displayed flow lines shows the path of individual particles through the left ventricle. In this representations the blood flow over the time space of a heart cycle is shown, and it may be seen that the blood is drawn in from the atrium, flowing downwards towards the apex and is finally pushed upwards in the systole to exit the left ventricle into the aorta. During this the blood describes a type of vortex movement. A data set, onto which these figures are based may be used as an input data set for the method of the invention.

Figure 2A:
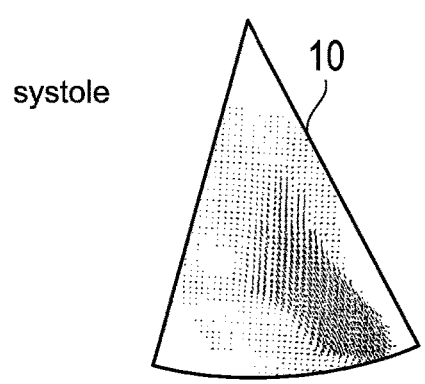
FIGS. 2A-2B show another representations of a velocity vector field through the left ventricle at systole (a) and diastole (b)
Figure 2B:
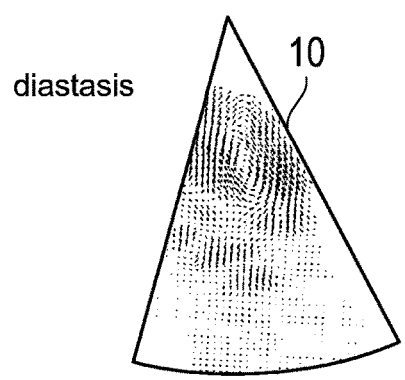

FIGS. 2A-2B show another approach for the representation of such a velocity vector field. Herein, a two dimensional lattice is represented, which correspond to the sound field of an ultra sound converter. An arrow is shown at each point of lattice grid, indicating the direction and size of the velocity. Every figure shows the state within a certain time frame during the heart cycle, FIG. 2A within the systole and FIG. 2B within the diastole. The respective gradient vector fields over the time frame or other above mentioned parameters may be calculated from a time series of such velocity vector fields.

Figure 3:
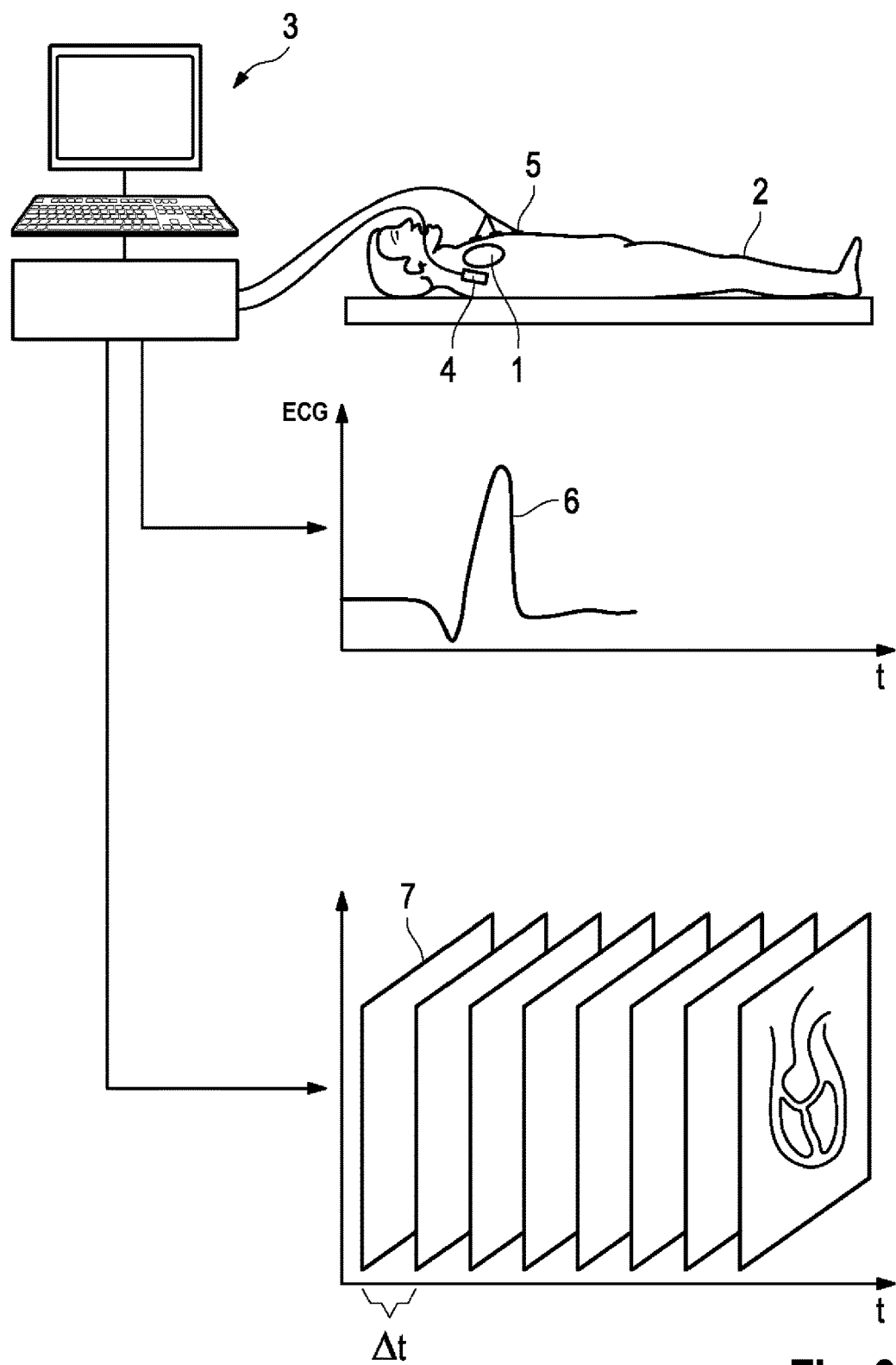
FIG. 3 is a schematic representation of a device for the acquisition of ultra sound images, from which a velocity vector field may be reconstructed.

FIG. 3 schematically shows a device 3, with which ultra sound images of the heart 1 of a patient are acquired. This is done by an ultra sound device 3, the sound head 4 of which in this case was inserted into the oesophagus of the patient, in order to acquire images as close as possible to the heart. Alternatively, the sound head may also be placed on the chest from the outside. Simultaneously, an ECG is acquired by means of electrodes 5. There are different known methods to acquire a four dimensional ultra sound image of the heart over one heart cycle, wherein the fourth dimension is the time. Thus, the result of the measure is a time series of ultra sound images 7, which at least cover one heartbeat, and having been acquired with an acquisition rate of $\Delta t$. $\Delta t$ thus corresponds to the time frame of each image. By way of the concurrent ECG 6 it is possible, to assign one specific point of time within the heart cycle to each ultra sound image 7. The ultra sound images 7 are digitally stored and are either 2D or preferably 3D.

From the velocity vector fields 10 for example pressure gradient vector fields for each time frame may be calculated. Simultaneously, it is useful to extract the boundary surface between the blood and heart chamber wall for the ventricle of interest from at least one or more or all ultra sound images 7 originally acquired, in order to be able to correlate the calculated gradient fields with the anatomy of the heart chamber.

Figure 4A:
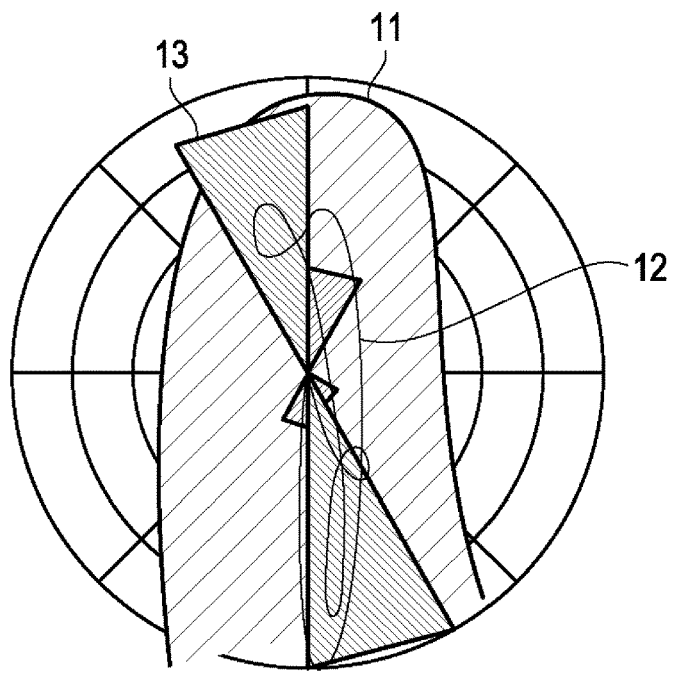
FIGS. 4A-4B are representations of the polar distribution of the pressure gradients in the left ventricle over one heartbeat, with the display of a section across the heart chamber contour being superimposed.

An appropriate representation of the invention is shown in FIG. 4A. This corresponds to a polar plot of each of the summed gradients, the input data set of which was a time series of 2D velocity vector fields. They were obtained from a time series of 2D ultra sound images, which were oriented along the longitudinal axis of a left ventricle. From one of these images the line 11 was obtained e.g. by segmentation, which is a section through the boundary surface between blood and tissue of the left ventricle, wherein the apex of the ventricle is approximately located at 0° in the polar diagram. The pressure gradients summed up for each time frame are each represented as a, the origin/center of which is in the center of the chamber. The apex is at 0°, the base is at 180°. Simultaneously, cake-wedge shaped bars are represented, each representing the sum of the pressure gradients located in this angle. It thereby becomes clear that the pressure gradients increasingly tend to either point towards the 0° direction or the 180° direction, i.e. the blood either enters into the left ventricle in the apex direction or (at a different point of time in the heart cycle) exits therefrom in the base direction or in the aortic valve direction. FIG. 4A thus shows the pressure slope of a normal heart, since there hardly are pressure gradients transversally to this main flow direction.

Figure 4B:
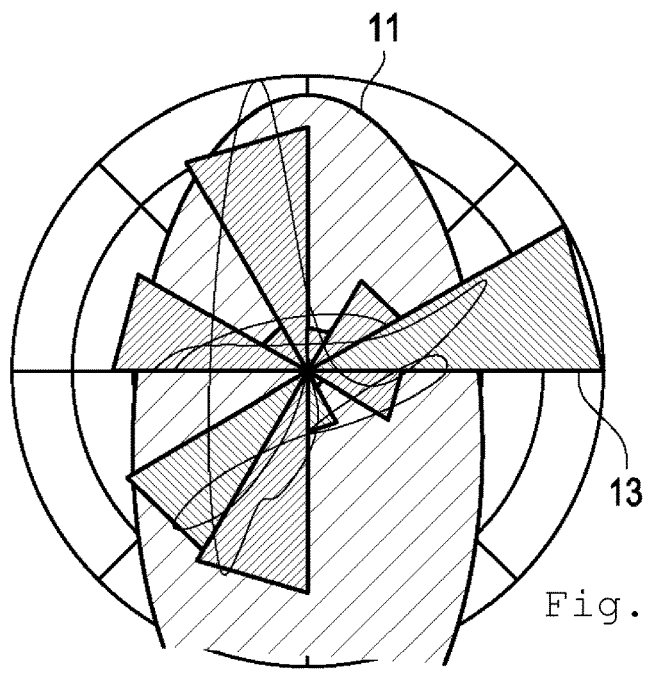

In FIG. 4B, on the other hand, this is different, large pressure gradients may also be seen in the 90° and 270° direction, such as it is represented by the respective bars. This indicates that the heart does not effectively generate pressure gradients, which are not for the pumping procedure of the heart, but are only for exerting pressure onto each of the opposite heart chamber wall. This may result in pathologic deformation of the heart chamber.

Figure 5:
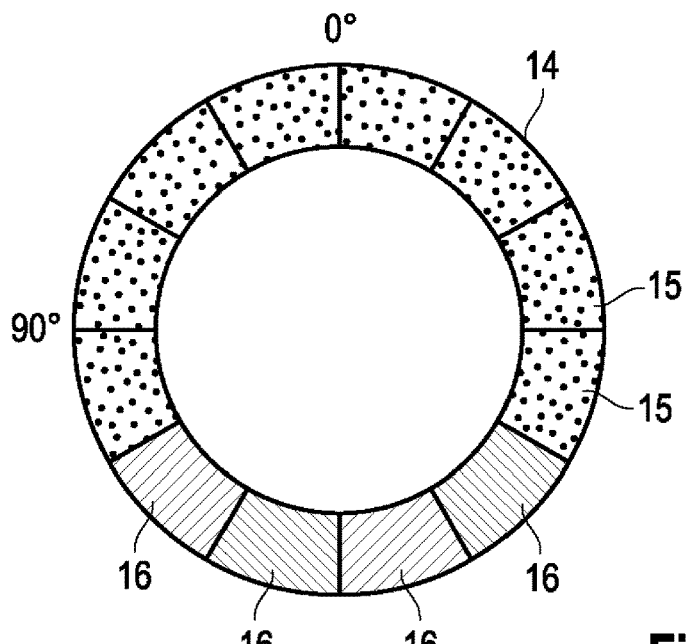
FIG. 5 is an alternative polar diagram of the summed gradient.

FIG. 5 shows another type of display, and shows an annular polar diagram 14, which is divided into segments 15. The segments are colored (colors or grey values), wherein the shade corresponds to the amount of the summed gradients pointing to that direction, which corresponds to the segment. Here again, the apex is at 0° and the base is at 180°. In this example the lower segments 16 at app. 180° are dark, thus indicating the summed gradients pointing towards this directions. In this case the summed gradients are only summed over the time frames, which are located within the systole, i.e. gradients such as e.g. the momentum point towards the aortic valve direction within the base.

Figure 6:
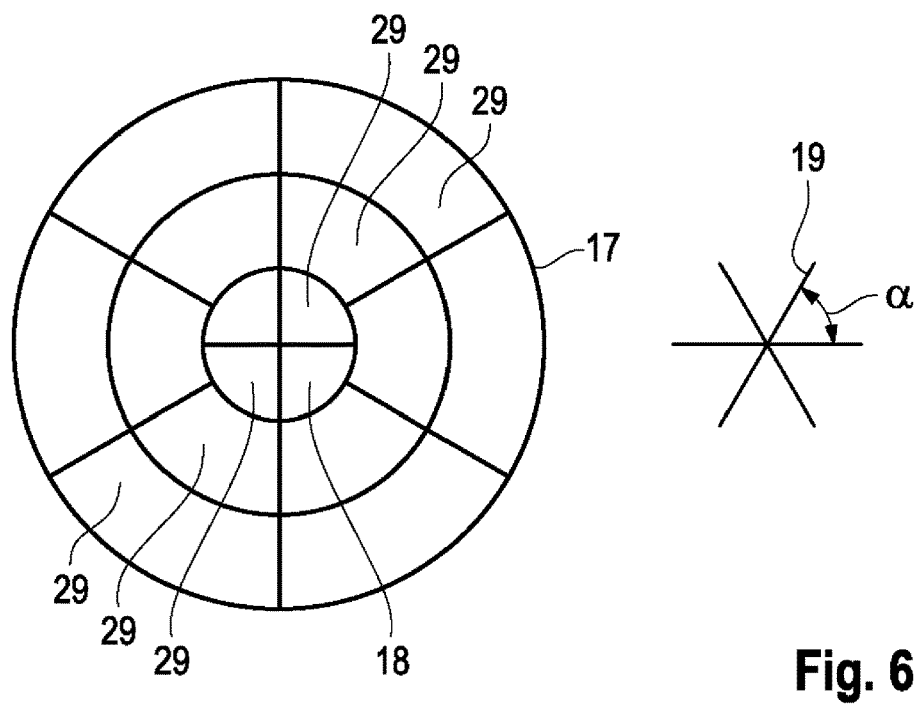
FIG. 6 is a representation of the summed gradient in the form of a standard polar diagram ("Bull's Eye")

FIG. 6 shows still another mode of representation, in this case as a standard polar plot, "Bull's Eye" diagram, which plot corresponds to a projection of the wall of a left ventricle onto a plane. The projection is divided into certain segments 17, not only in the circumferential direction, but also in the radial direction. The outer segments are in the vicinity of the base, the inner segments 18 are at the apex. This polar plot, too, may have (color-) shades, which correspond to the amount or the intensity, respectively, of the respective summed gradients starting from the center of the left ventricle point towards the direction of the endocardium which corresponds to this segment. Such a polar plot contains 3D information—however, they may also be obtained from three or more 2D velocity vector fields 19 which each are parallel to the long n axis of the ventricle, but which enclose an angle $\alpha$ with each other. In three 2D planes a is preferably about 60°. In doing so, sufficient space information about the gradients are acquired, to fill the segments of the polar plot. The summed gradients of the velocity vector field indicated by 19 are e.g. inserted into the segments 29 of the polar plots 17.

Figure 7:
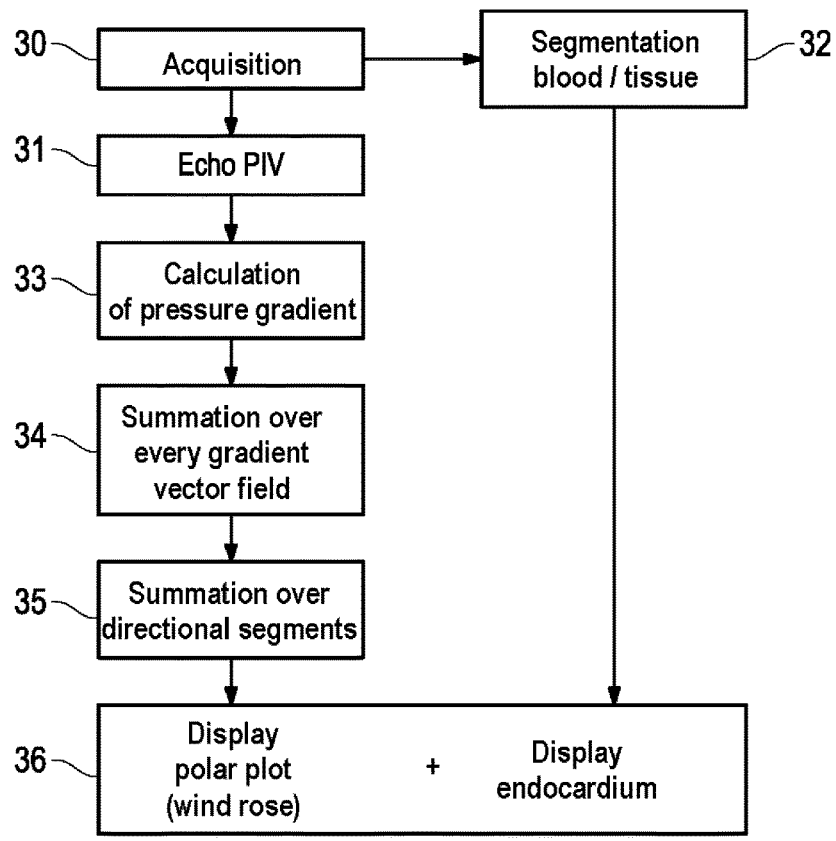
FIG. 7 is a flow diagram of the method of the invention.

FIG. 7 shows a flow diagram of one embodiment of the method of the invention.

Initially (step 30), images of the heart are acquired, preferably ultra sound images. This is preferably done dynamically, i.e. a time series of images of the heart is acquired, covering the state of heart movement over multiple time frames within a heart cycle.

From these images a velocity vector field for each time frame is calculated by way of PIV (Particle Image Velocimetry) (step 31). Furthermore in step 32, the boundary surface between blood and tissue is segmented from the images and the images are stored.

In step 33 the respective pressure gradient vector fields—or other parameters, as described above, are calculated from the velocity vector fields.

In step 34 the gradients are summed over each gradient vector field, so that now only one pressure gradient per time frames is deposited. Optionally, they are summed up for certain segments of the space directions (step 35), to further reduce the data, thereby making them displayable with greater ease. Subsequently, in step 36 representation is performed such as in FIGS. 4A-4B, of a wind rose type. There, the summed up pressure gradients are initially represented as bars in a polar plot. Simultaneously, the endocardium or the boundary surface between blood and the endocardium, respectively, is superimposed, in order to correlate the space orientation of the pressure gradients to the heart chamber.

Figure 8:
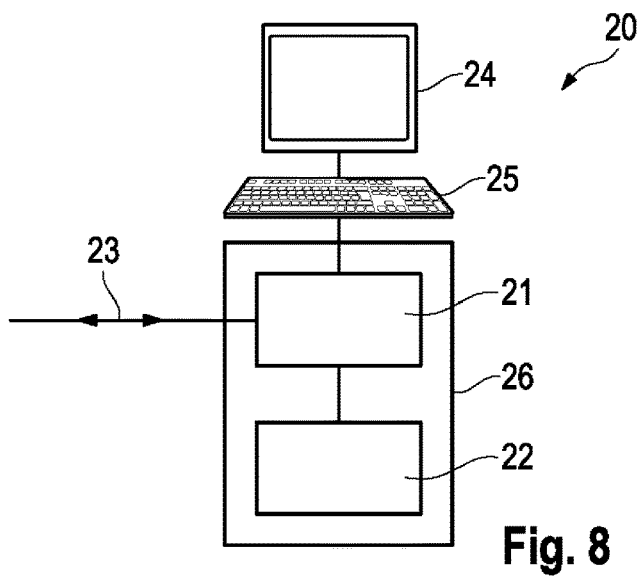
FIG. 8 is a schematic image of the device of the invention.

FIG. 8 finally shows a device, with which the method of the invention may be performed. It is a computer 20 having a screen 24 and an input device, especially a key board 25. The computer 26 itself consists of at least one data storage 22 and CPU 21. They are connected to the internet or an acquisition device 3 for recording the ultra sound images via a data cable 23. The screen 24 is for displaying the resulting images, such as e.g. in FIGS. 4A-4B. The computer may be operated via the key board 25. The images, both the input data set and the calculated images, are stored in the memory 22 and are calculated by the CPU 21.

The invention claimed is:

1. Method for analysis and display of blood flow information, the method comprising:
providing, to a computer, a digital input data set comprising a time series of 2D or 3D velocity vector fields, wherein each velocity vector field represents a velocity of blood flow within a blood vessel of a heart chamber or part thereof in a certain time frame within a heart cycle,
calculating a gradient-vector field for every time frame from a time series of velocity vector fields, wherein the gradient vector field is a vector field of gradient vectors of any vector quantity that can be calculated from the velocity vector fields;
summing the gradient vectors over an entirety of the gradient vector field, or a part of the gradient vector field, within one time frame to generate a summed gradient vector for each time frame; and
displaying, on a screen, the summed gradient vectors with reference to their directions in space within the blood vessel.

2. The method of claim 1, wherein the summed gradient vectors of all or part of the time frames of the heart cycle are displayed in a diagram and are analyzed with reference to their space directions within a heart chamber.

3. The method of claim 2, wherein the summed gradient vectors of those timeframes, of which the input data sets were acquired during systole or diastole, respectively, are displayed in one diagram.

4. The method of claim 2, wherein the summed gradient vectors of all or part of the time frames of a heart cycle are displayed in one or several polar diagrams, wherein the angles of a polar diagram represent the space directions of the heart chamber, in which the gradient vectors are pointing.

5. The method of claim 4, wherein a circumference of the polar diagram is divided into angular segments, and in each segment, the sum of all summed gradient vectors pointing in the direction of this segment, are displayed as bar or as grey shade or color shade, wherein the height of the bar or the shade corresponds to the modulus of the sum of all summed gradient vectors pointing in the direction of this angle segment.

6. The method of claim 4, wherein the space directions of the summed gradient vectors are represented in one or two polar diagrams, wherein each polar diagram corresponds to the space directions of the heart chamber projected onto one plane.

7. The method of claim 1, wherein the gradient vector field is selected from a group consisting of a pressure gradient, a gradient of kinetic energy, a momentum, a convective component of momentum, and an inertial component of momentum of blood flow.

8. The method of claim 7, wherein the pressure gradient vector field for each time frame is calculated by:

calculating a derivative with regard to time of the velocity vector fields from one time frame to the next and storing a result as a time series of acceleration vector fields;
for each time frame, calculating the gradient of the velocity vector field and storing the result as a time series of velocity gradient matrices;
for each time frame, calculating a scalar product between the velocity vectors and the velocity gradient matrices, and storing the result as a time series of calculated vector fields; and
spatially summing up the vectors within each calculated vector field.

9. The method of claim 8, wherein the step of spatially summing up the vectors within each calculated vector field is carried out with different weights.

10. The method of claim 7, wherein the pressure gradient vector field is computed by solving a pressure Poisson equation with boundary conditions.

11. The method of claim 7, wherein the pressure gradient vector field for each time frame is calculated by:
for each time frame, calculating the gradient of kinetic energy;
for each time frame, calculating a product between the velocity vector field and a rotation of the velocity vector field; and
summing up the calculated vector fields with different weights.

12. The method of claim 1, wherein the gradient vectors are summed up over that part of the gradient vector field which depicts the blood vessel, the heart chamber, or a predetermined section of the heart chamber.

13. The method according to claim 1, including a step of acquiring ultrasound data from a human or animal body and obtaining the input data from the ultrasound data acquired, wherein the display of the summed gradient vectors is done within less than 1-5 seconds after the acquisition of the ultrasound data.

14. The method of claim 1, including a step of acquiring a time series of ultrasound images of the heart, wherein each ultrasound image is acquired during a time frame within the heart cycle, wherein the input data set is obtained by means of digital particle image velocimetry from the time series of ultrasound images of the heart.

15. The method of claim 14, wherein a heart chamber is segmented within the time series of ultrasound images of the heart, and the velocity vector fields are reconstructed for the segmented heart chambers.

16. The method of claim 1, wherein the digital input data set comprises one, two or three two-dimensional velocity vector fields for each timeframe wherein the two-dimensional velocity vector fields each depict the velocity of the blood flow within a separate image plane through the blood vessel.

17. The method of claim 16, wherein the summed gradient vectors for each two-dimensional velocity vector fields are displayed in an individual polar diagram.

18. The method of claim 17, wherein the summed gradient vectors are obtained from three two-dimensional velocity vector fields, which are oriented each along a long axis of a left ventricle.

19. The method of claim 1, wherein each velocity vector field displays the velocity of blood flow within a left ventricle, and wherein the summed gradient vectors are displayed in a standard "Bulls's Eye" polar diagram, a centre of which shows a modulus of the summed gradient vectors pointing in the direction of an apex, in a color shade.

20. The method of claim 1, wherein the summed gradient vectors of all timeframes are displayed one after the other in a sequence of the summed gradient vectors within the heart cycle.

21. The method of claim 1, wherein one or several ultrasound images of a blood vessel are analyzed by segmenting into blood and tissue of a wall of the blood vessel, and wherein a space direction of the summed gradient vectors are referenced to the blood vessel wall and/or displayed with reference to the blood vessel wall or wherein an angle between the summed gradient vectors and the blood vessel wall is analyzed.

22. Non-transitory data carrier containing a computer program for performing the all method steps according to claim 1, when the computer program is executed on a computer.

\* \* \* \* \*